United States Patent [19]
O'Connor

[11] 3,942,001
[45] Mar. 2, 1976

[54] INSPECTION OF CONTAINERS
[75] Inventor: Bartholomew John O'Connor, Churchtown, Ireland
[73] Assignee: Talcoma Teoranta, Dublin, Ireland
[22] Filed: June 26, 1974
[21] Appl. No.: 483,350

[30] Foreign Application Priority Data
June 27, 1973   Ireland.................................. 488/73
May 14, 1974   Ireland................................ 1036/74

[52] U.S. Cl. ........ 250/223 B; 209/111.7 T; 250/224
[51] Int. Cl.[2]......................................... B07C 5/342
[58] Field of Search ............ 250/223 B, 221, 222 R, 250/224; 209/111.7

[56] References Cited
UNITED STATES PATENTS
3,415,370   12/1968   Husome ...................... 250/223 B X
3,662,883   5/1972.   Sager............................... 209/111.7
FOREIGN PATENTS OR APPLICATIONS
1,206,136   9/1970   United Kingdom............. 250/223 B Primary Examiner—James W. Lawrence
Assistant Examiner—E. R. LaRoche
Attorney, Agent, or Firm—Sughrue, Rothwell, Mion, Zinn & Macpeak

[57] ABSTRACT

Apparatus for detecting the presence of extraneous matter and/or cracks in translucent containers and in particular translucent containers when the colour density and/or wall thickness of the translucent containers vary significantly from container to container which includes a vertical spot beam of light which is projected through the container to generate an electrical inspection signal corresponding to the amount of light passing through the container. This electrical inspection signal is compared with a predetermined electrical acceptance signal, which is a function of the vertical position of the spot beam of light relative to the container. There is an ambient light correction and for colored containers either the inspection signal or the acceptance signal is altered during the inspection process to take account of the colored density and/or wall thickness.

54 Claims, 10 Drawing Figures

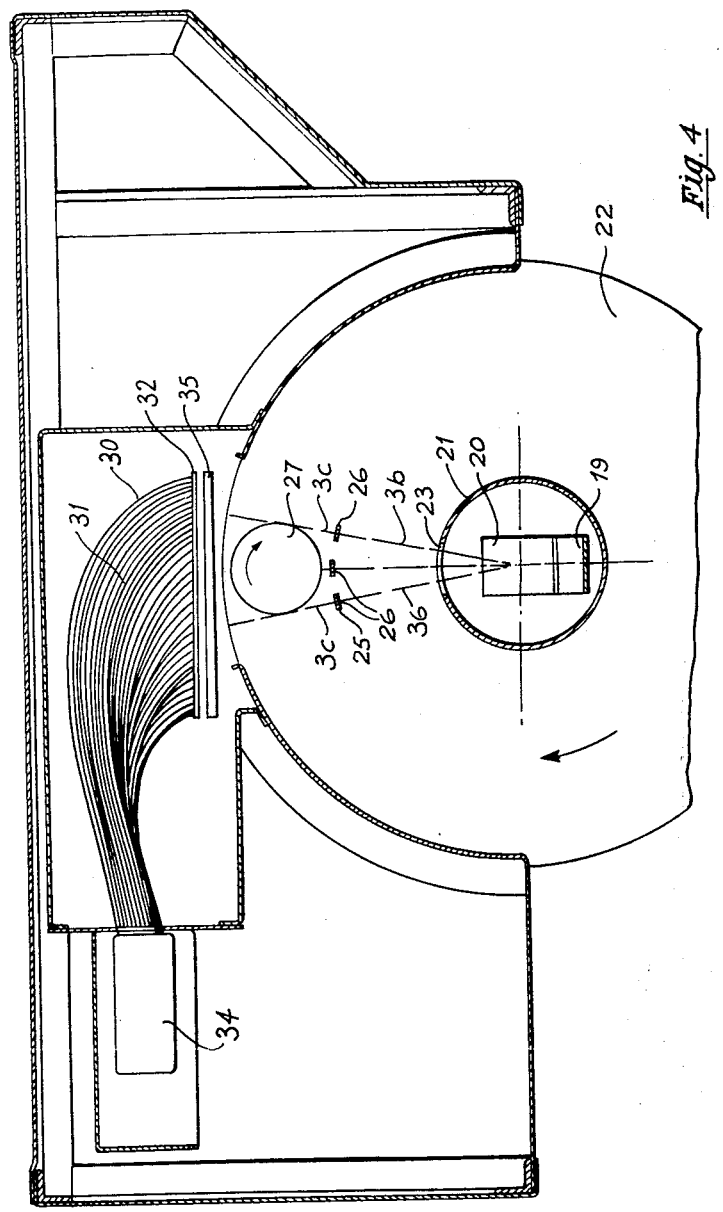

INSPECTION OF CONTAINERS

BACKGROUND OF THE INVENTION

1. Field of the Invention

This invention relates to a method and apparatus designed for inspecting translucent containers for the presence of extraneous matter and/or cracks. The invention is particularly suitable for use with translucent containers when the colored density and/or wall thickness of the translucent containers vary significantly from container to container.

2. Description of the Prior Art

It is known for example in U.S. Pat. No. 3,245,532 (Quinn) to provide an inspection apparatus for detecting an uneveness in the surface of an article in which beams of light are directed on separate portions of the surface of the article and the amount of light transmitted from the container is detected. U.S. Pat. No. 2,750,519 (Summerhayes et. al.) describes a method for inspecting the interior surfaces of open ended containers by means of radiant energy.

U.S. Pat. No. 2,593,127 (Fedorchak) also describes apparatus for inspecting the inner surface of a glass container by means of a light source and reflectors. Unfortunately thse and other apparatus known already suffer from major disadvantages.

Firstly, no attempt has been made in any of these known constructions of inspection apparatus to correct for variations in ambient light which would inevitably distort the response of the apparatus. Further, the quantity of light transmitted through for example, a bottle will vary between the bottom of the bottle, the neck of the bottle and the shoulder of the bottle. Thus if one measures the amount of light transmitted through the container and rejects the container when the amount of light transmitted is below a fixed amount it is possible not to detect cracks or occlusions. Further, it will be appreciated that in the case of an inspection apparatus designed to handle containers made from colored glass some provision must be made to compensate for the variations in overall light transmission which will occur from one container to the next due firstly, to variations in the color density from container to container and secondly due to variations in wall thickness from one container to another.

OBJECTS

The present invention is directed towards providing an apparatus and method for detecting the presence of extraneous matter and/or cracks in translucent containers which will correct for the normal variations in light transmission that will occur when light is transmitted through a container of non-uniform shape.

Another object of the invention is directed towards providing an apparatus and method for detecting the presence of extraneous matter and/or cracks in translucent containers when the color density and/or wall thickness of the translucent containers vary significantly from container to container.

A further object of the invention is directed towards providing an apparatus and method for detecting the presence of extraneous matter and/or cracks in translucent containers the response of the apparatus being unaffected by ambient light.

A still further object of the present invention is to provide an efficient light collection apparatus for use with an inspection apparatus such as that of the present invention.

SUMMARY

According to the invention there is provided:

apparatus for detecting the presence of extraneous matter and/or cracks in translucent containers, said apparatus comprising;

an inspection zone;

means for rotating a translucent container within the inspection zone;

means for providing a spot beam of light adapted for scanning vertically in the inspection zone;

a light collection apparatus in the inspection zone;

means for generating an electrical inspection signal corresponding to the amount of light passing through the translucent container and impinging on the light collection apparatus;

means for comparing said inspection signal with a predetermined electrical acceptance signal, the value of said acceptance signal being a function of the vertical position of the spot beam of light relative to the container; and means for generating a rejection signal when the intensity of light passing through the translucent container is below a predetermined value measured by the said acceptance signal.

Further, the invention provides:

apparatus for detecting the presence of extraneous matter and/or cracks in translucent containers when the color density and/or wall thickness of the translucent containers vary significantly from container to container, said apparatus comprising;

an inspection zone;

means for rotating a translucent container within the inspection zone;

means for providing a spot beam of light adapted for scanning vertically in the inspection zone;

a light collection apparatus in the inspection zone;

means for generating an electrical inspection signal corresponding to the amount of light passing through the translucent container impinging on the light collection apparatus;

means for comparing said inspection signal with a predetermined electrical acceptance signal;

means for obtaining prior to inspection of a container, a sample inspection signal at a predetermined vertical position of the spot beam of light;

means to adjust the said sample inspection signal or the corresponding acceptance signal to an appropriate signal value while still maintaining a desired ratio between the inspection signal and the acceptance signal at that vertical position of the spot beam of light, the ratio of the original signal to the adjusted signal providing an adjustment factor; and means to adjust the inspection signal or acceptance signal by the adjustment factor during the inspection of the container.

Further, the main advantage of the present invention is that it provides an extremely efficient bottle inspection apparatus. Further, the present invention provides a bottle inspection apparatus that can be used with colored glass containers which has not heretofore been possible.

DESCRIPTION OF DRAWINGS

FIG. 4 is a plan cross-sectional view along the lines IV—IV of FIG. 1.

DESCRIPTION OF THE PREFERRED EMBODIMENTS

Figure 5:
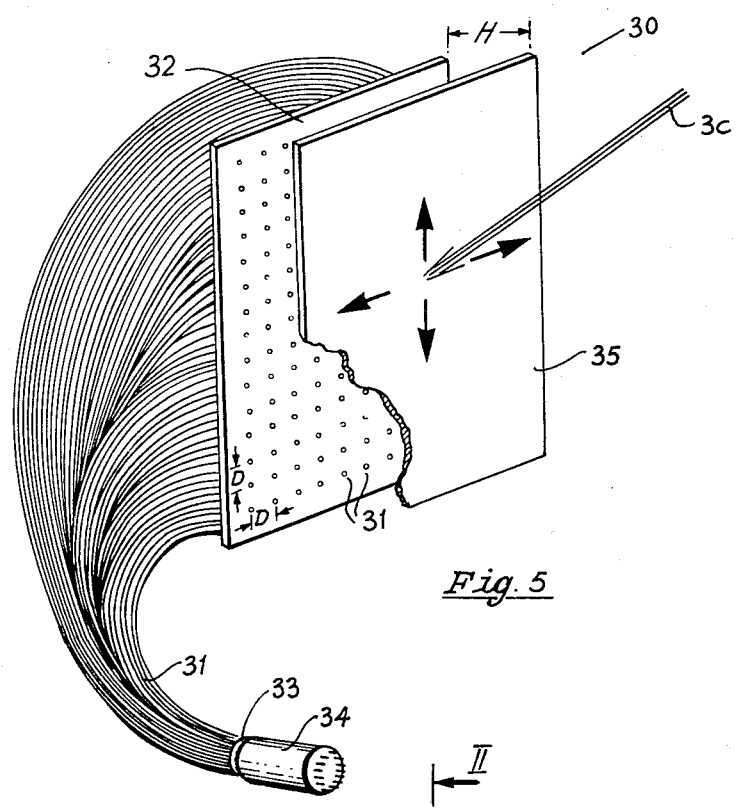
FIG. 5 is a perspective partially diagrammatic view of portion of the light collection apparatus incorporated in the invention.
Figure 1:
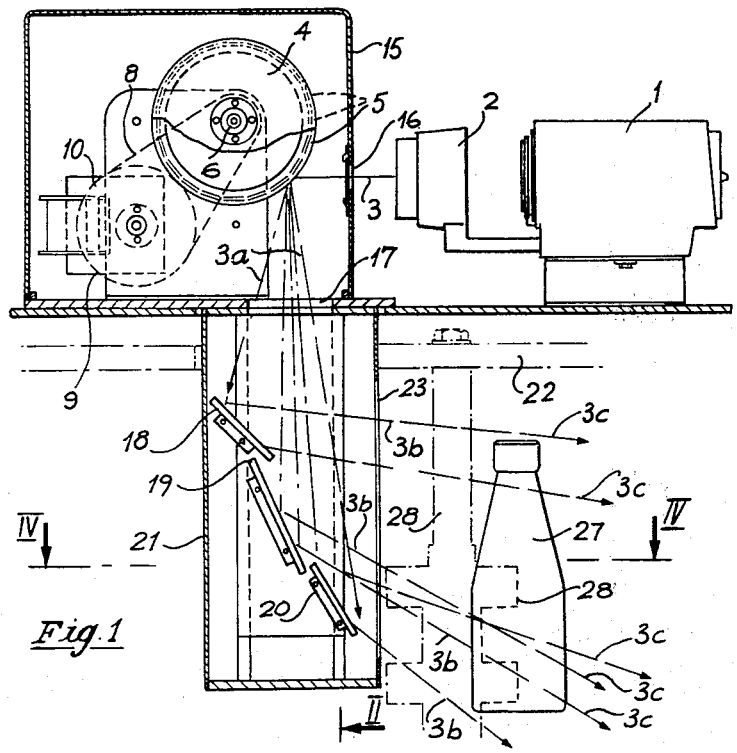
FIG. 1 is a side, partially cross-sectional, elevation of the apparatus according to the invention.

Referring to the drawings, and initially to FIGS. 1 to 4 thereof, the apparatus comprises a light projector 1 and an associated condenser 2 for producing a concentrated narrow slit or ribbon of light 3.

The ribbon of light 3 is projected onto a rotating drum 4 which tangentially supports twenty outwardly reflecting plane silvered mirrors 5, each of which is 1 inch in axial length and ¾ of an inch in width. The drum 4 is fixedly mounted upon a shaft 6 carrying a pulley 7 driven by a belt 8 (see FIG. 3), coupled to the pulley 9 of an electric motor 10, the drum 4, electric motor 10, and associated mechanism being mounted within a casing 15 having an aperture 16 permitting entry of the ribbon of light 3 through the casing 15 to the mirror carrying drum 4.

As the ribbon of light 3 impinges upon each of the rotating mirrors 5, it is reflected downwardly through an aperture 17 in the floor of the casing 15 to three plane silvered mirrors 18, 19 and 20, thereby providing a repetitive scanning ribbon of light 3a.

The reflected ribbon of light 3a is further reflected from the mirrors 18, 19 and 20 which are angularly mounted within a vertically disposed column 21 located below the casing. A rotating table 22 (only shown in part and by interrupted lines in FIGS. 1 and 3) encircles the column 21. The column 21 has a vertical slot 23 permitting exit of the further reflected ribbon of light 3b from the column 21.

It will be appreciated that for example due to the relative disposition of the mirrors 18, 19 and 20 that a ribbon of light 3b when projected from the top of the mirror 19 will in fact be deflected at a flatter angle to the horizontal than the beam 3b as it left the bottom of the mirror 18. There is thus a slight overlap of the ribbon of light 3b being reflected from the column 21.

The inclination of each of the mirrors 18, 19 and 20 to the vertical axis of the column 21 is so arranged as to ensure that the spot beam of light which is subsequently produced, impinges on a translucent container at the most effective angle of incidence. It will be appreciated that internal reflection of light within the container may cause errors in response. Further, it is important to ensure that critical areas of the container are sufficiently scanned and hence an overlap, as described above, during the vertical scan may be desirable.

Figure 3:
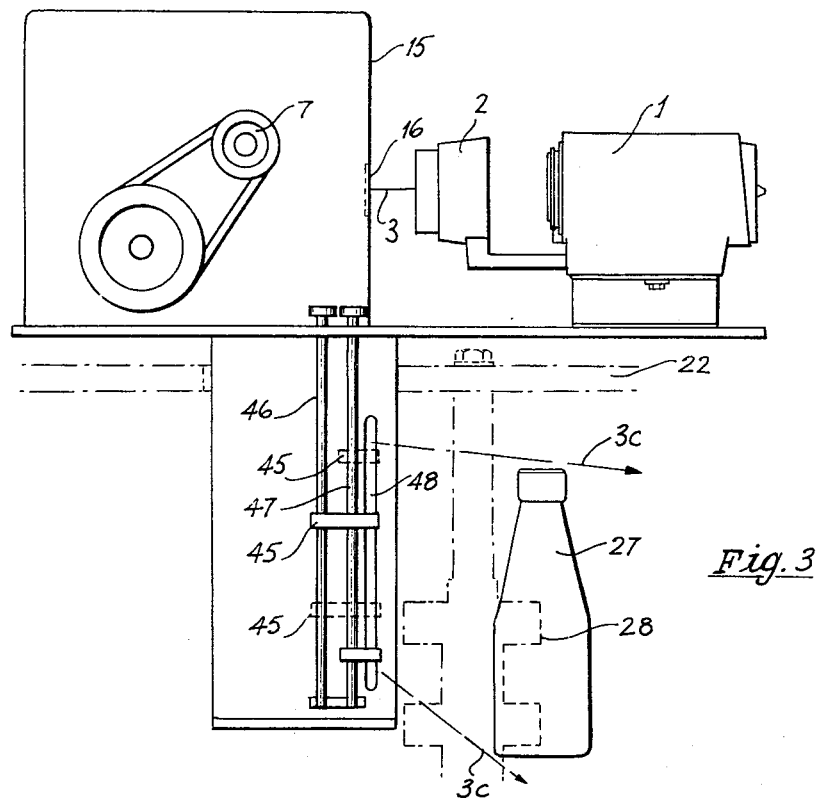
FIG. 3 is a side elevation of portion of the apparatus.
Figure 2:
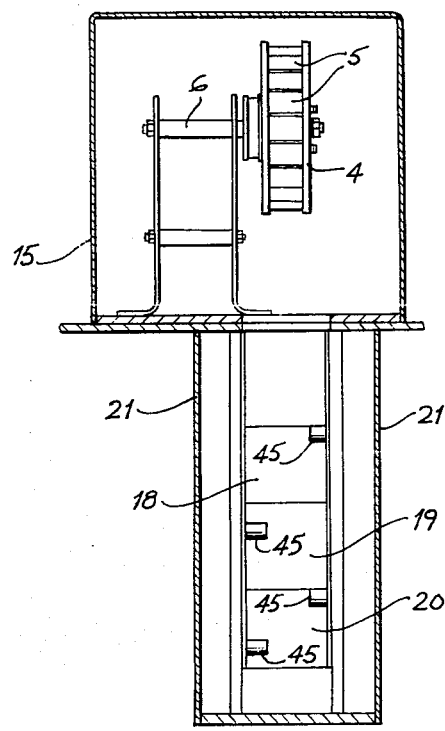
FIG. 2 is a cross-sectional view along the lines II—II of FIG. 1.

Referring to FIG. 3, photosensors 45, conventionally mounted on lead screws 46 and 47, project into the column 21 through a slit 48. The photosensors 45 are operatively connected to the control apparatus as will be described hereinafter. The photosensors 45 are so positioned that they intercept the outer edges of the scanning ribbon of light 3b reflected from the plane mirrors 18, 19 and 20. It will be appreciated that the vertical positions of the photosensors 45 on the column 21 are adjusted by the lead screws 46 and 47.

Supported by the rotating table 22 is a vertical masking member 25 having a vertical slit 26 (shown in three positions in FIG. 4), which serves to occlude all but a portion of the repetitive ribbon of light 3b thereby concentrating the latter into a narrow spot beam of light 3c which passes through an angle of 20° (see FIG. 3) as the table 22 and slit 26 are rotated. Thus the concentrated spot beam of light, hereinafter referred to as the scanning beam 3c, scans through an angle in a vertical plane and moves through an angle in a horizontal plane. It will, of course, be understood that the position of the slit 26 relative to a bottle 27 remains constant, i.e. in the centre position shown in FIG. 4.

The bottle 27 to be inspected is carried around the periphery of the rotating table 22 by fingers (not shown) serving to press the bottle 27 against rotating rollers 28 which revolve the bottle 27 as it passes through the scanning zone penetrated by the concentrated scanning beam 3c the latter being focussed substantially on the axis of the bottle 27. Light passing through the bottle 27 is collected by a light collection apparatus indicated generally by the reference numeral 30 associated with a photo-multiplier 34 which feeds a signal to a control circuit (see FIG. 6). The light collection apparatus 30, and the control apparatus will be described in more detail below.

Referring to FIG. 5 there is illustrated the light collection apparatus 30 which includes a number of fiber optic elements 31 mounted in a matrix arrangement on the front surface of a platform 32. The fiber optic elements 31 are mounted in the form of a regular square matrix of side length D, part of such a matrix is shown in FIG. 5. The other ends of the fibers are taken together to form a bundle 33, the end face of which is suitably shaped, optically polished and optically coupled to a photosensor element 34, namely, a photomultiplier tube. A light diffusing screen 35 in this embodiment, a sheet of flashed opal glass is placed at a distance (H) in front of the platform 32.

As will be appreciated, the scanning beam 3c suffers refraction and reflection on passing through the bottle 27 but for each of illustration FIG. 5 shows the scanning beam 3c as a relatively narrow beam of light falling upon the diffusing screen 35 after passing through the bottle 27.

The scanning beam 3c moves up and down and across the surface of the diffusing screen 35 and to correct a decrease in response as it approaches the edge of the screen, mirrors (not shown) are placed at the perimeter of the platform 32 with their reflecting surfaces normal to the front surface of the platform and facing inward across the matrix of fiber optic elements.

The light collecting apparatus 30 described herein, consists of 247 plastic fiber optic elements, each 60 Cm. long and 0.06 inches in diameter, arranged in a regular 13 × 19 matrix with 2 Cm. spacing between elements. The front portions of the elements are fixed by suitable fasteners in a sheet of black nylon measuring 28 Cm × 40 Cm × 0.25 inches thick.

The nylon matrix platform is mounted in a shallow sided rectangular box frame, parallel with and separated 4 Cm from a screen of flashed opal glass measuring 28 Cm × 40 Cm. The four inner surfaces of the mounting frame between the matrix platform and the diffusing screen have front-silvered mirrors fitted to them to provide correction of edge effects as described above. The rear portions of the plastic fiber optic elements are tightly bundled, the end face of the bundle is shaped, optically polished, and placed approximately 5 mm from the photocathode surface of a 50 mm photomultiplier tube 34.

The performance of the light collection apparatus may be adjusted by appropriate variation of the parameters such as the number, cross-sectional area and spacing of the individual fiber optic elements in the matrix, the distance between the front portions of the elements and the diffusing screen and the diffusing characteristics of the screen itself.

In certain applications it may be desirable for the apparatus to have a graded or locally non-uniform response to incident light. This may be achieved by suitable modification of the spacing of the fiber optic elements of uniform cross-section in the matrix, that is to say, by making (D) a variable depending on the location in the matrix of the elements being considered or, alternatively, by appropriately grading the cross-sectional areas of the fiber optic elements in the matrix.

In operation, the inspection apparatus according to the invention is located adjacent or in the path of a conveyor line (not shown) carrying bottles to be inspected. Bottles to be inspected are fed to the rotating rollers 28 against which the bottles are held and rotated while the table 22 is revolving.

It will be understood that during the scanning period, the scanning beam 3c passing through the masking slit 26 continuously scans in a vertical plane, and simultaneously it is caused to move in a horizontal plane by rotary movement of the masking member 25. Further, the bottle 27 is continuously rotated during transmit thereof transit the scanning zone, and the scanning rate is so arranged that the entire area of the bottle is overscanned by 25 percent. The scanning rate and the rotation of the bottle are synchronized so that there is a 10 percent overlap between successive scans.

Should the amount of light falling upon the light collection apparatus 30 be reduced, below a predetermined level by virtue of the spot or beam of light being partially or wholly obstructed or absorbed by extraneous matter in the bottle 27, the output from the photomultiplier 34 will be reduced, thus generating an electrical rejection signal indicative of the presence of the extraneous matter in the bottle 27. The rejection signal thereby generated is fed to actuate a rejection mechanism such as described in our British Pat. Specification No. 1,206,136, which diverts the bottles 27 from the return path to the conveyor line (not shown).

It will be appreciated that the successful operation of the inspection apparatus according to the present invention requires that the various operations be synchronized and controlled. Some inspection apparatus functions must be synchronized with the rotation of the rotating table 22, that is to say, with the translation of the bottle 27 from the input feed through the inspection zone to the output feed. Other functions must be synchronized with or controlled by the position of the scanning beam relative to the bottle 27 being inspected. How these synchronizations and control signals are obtained and processed is described below.

Control signals relating to the rotation of the table 22 are it will be appreciated, readily obtained in conventional manner from any form of timing unit 69 (see FIG. 6), for example, electronic sensors which are placed around the circumference of an appropriate rotating disc having as many teeth or apertures in the periphery as there are bottle positions on the rotating table 22, for example, in the present embodiment the disc, not shown, has eight teeth and is driven through a one to one gear train from the rotating table 22. Consequently, as each bottle 27 is traversed around the table, the necessary number of output pulses are generated. These timing pulses are identified by the reference letters TP and an appropriate reference numeral in the description below. Precise operation of these timing pulses can be set by appropriate adjustment of the peripheral position of the sensor relative to the disc.

The timing unit is used to provide signals to control the following functions:
1. Angular extent of the inpsection zone during which a bottle is examined.
2. Clocking of stored reject signal through a shift register memory prior to actuating the reject mechanism.
3. Actuation of the reject mechanism at exactly the appropriate time to ensure correct mechanical synchronisation.

It is always necessary to identify the start and end of the desired scan of a bottle so that the inspection operation may be activated during and only during this period. In addition, since it will be appreciated that it may be required to have different acceptance levels for different vertical positions of the scanning beam, it is necessary to provide control signals which are required to activate switches to make the necessary difference in acceptance voltages as will be described below. Appropriate signals for all these purposes are derived from the photosensors 45 as hereinafter referred to as scan related signals and identified by the reference letters SP and appropriate numerals.

Prior to considering the question of the operation of the apparatus according to the present invention, it is advantageous to consider briefly the problems involved in the inspection of a translucent container to detect the presence of extraneous matter and cracks. It will be appreciated that the signal output from the photo-multiplier 34 will vary in magnitude depending on the amount of light transmitted through the bottle 27.

Figure 8:
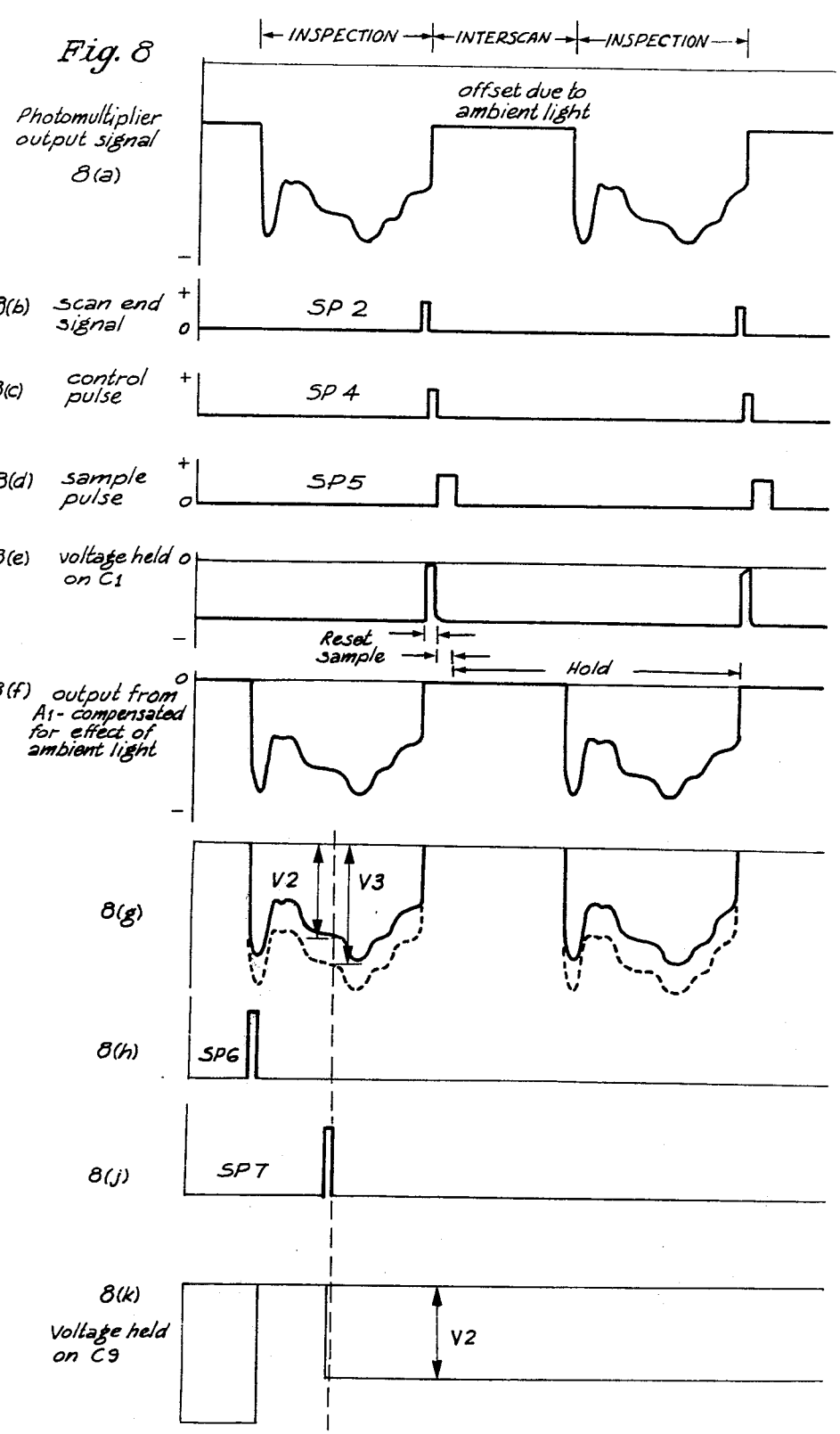
FIG. 8 is a diagram of some typical scan signals and some control signals.

Referring to FIG. 8a, the output signal from the photo-multiplier 34 can be resolved into two components, one consisting of the voltage generated by the scanning beam 3c which has passed through the bottle 27 and the other due to stray ambient light which will have leaked through the light shielding arrangement and which will cause the amount of light transmitted to the photo-multiplier 34 to be increased as shown. It will be appreciated that this offset signal due to the ambient light will vary depending on the intensity of such ambient light. FIG. 8 (f) illustrates the photo-multiplier output signal with the ambient light component eliminated. How the ambient light component is eliminated will be described hereinafter.

Figure 9:
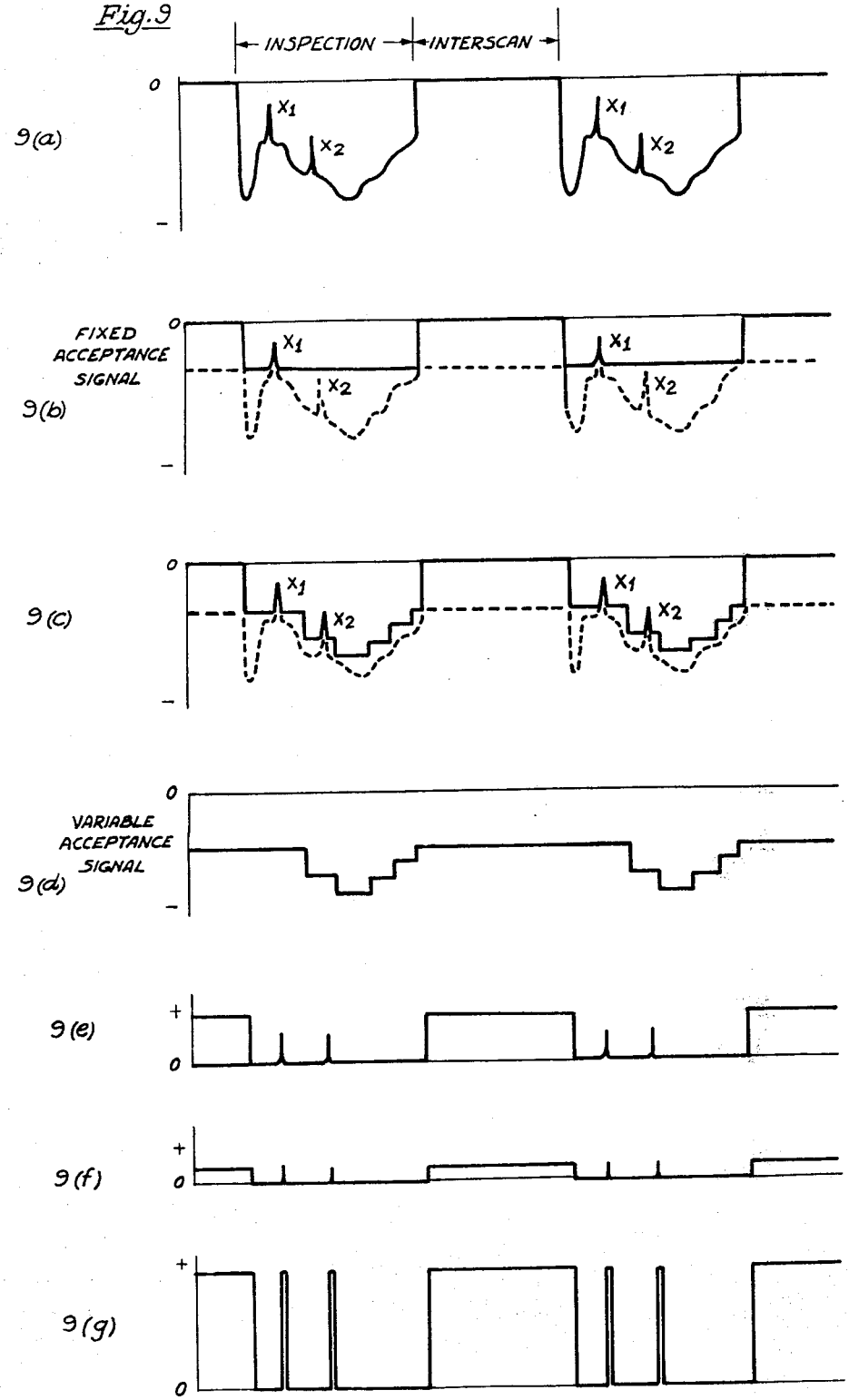
FIG. 9 is a diagram of some scan and other signals generated in the control circuits.

Referring to FIG. 9 (a) there is illustrated the output signal of the photo-multiplier 34 corrected for ambient light. This signal shows the effects of two occlusions or cracks causing peaks X1 and X2; strictly these peaks X1 and X2 are in fact valleys as the signal is negative. To identify these peaks X1 and X2 in the scanning or inspection signal, it is necessary to compare the inspection signal with some predetermined acceptance signal. How this acceptance signal is obtained in practice will be described hereinafter.

Referring to FIG. 9 (b), there is illustrated the inspection signal of FIG. 9 (a) with a constant acceptance voltage superimposed on it. It will be noted that this constant acceptance voltage will allow one of the occlusions or cracks namely, that causing the peak X1 to be detected while the other causing the peak X2 will escape undetected.

Referring to FIGS. 9 (c) and 9 (d), it will be appreciated that a variable acceptance signal such as illustrated in FIG. 9 (d) would be more preferable than the constant acceptance signal illustrated in FIG. 9 (b). FIG. 9 (c) illustrates this variable acceptance signal superimposed on the inspection signal. Both of the peaks X1 and X2 and accordingly the occlusions or cracks causing such peaks in the inspection signal are identified. It will be appreciated that the main reason for having a variable acceptance signal is that the quantity of light transmitted through, for example, a bottle will vary between the bottom of the bottle, the neck of the bottle and the shoulder of the bottle. Thus a variable acceptance signal is not necessary where the variation in light transmission over a translucent container between one portion of it and another does not vary significantly.

It will also be appreciated that in the case of an inspection apparatus designed to handle containers made from colored glass, additional processing of the inspection signal may be necessary. With such containers provision must be made to compensate for the variations in overall light transmission which will occur from one container to the next, due firstly, to variations in color density from container to container and secondly, due to variations in wall thickness from one container to the next.

FIG. 8 (g) illustrates the inspection signal that would be obtained from two similar bottles having slightly different color densities.

Figure 6:
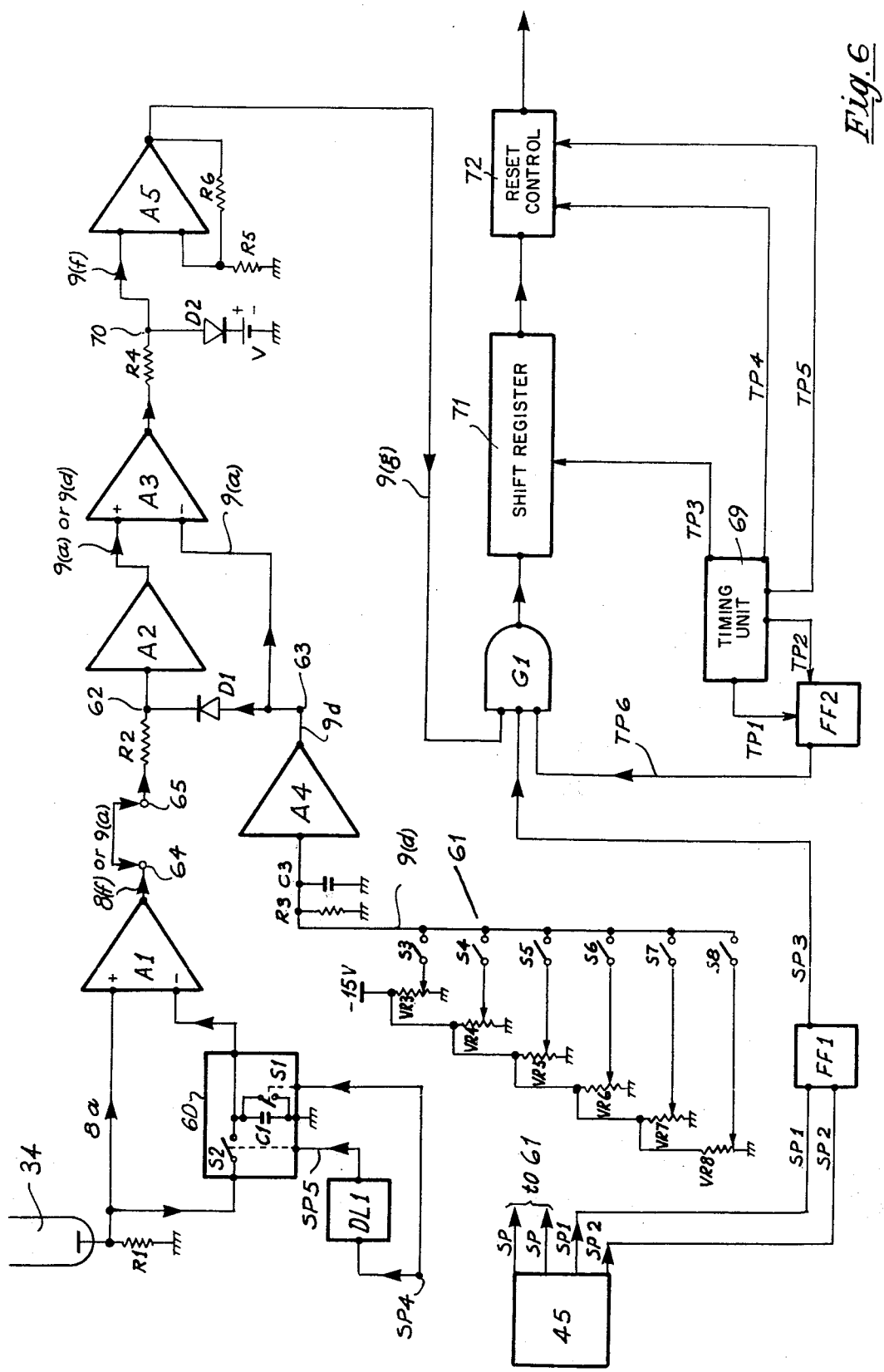
FIG. 6 is a circuit diagram of portion of the control equipment.

Referring to FIG. 6, the inspection signal generated across the load resistance R1 of the photo-multiplier 34 is illustrated in FIG. 8 (a), this signal 8a and is fed to a differential amplifier A1. For simplicity in the description, the various signals generated in the apparatus are identified by the Figure in which they are illustrated. A control pulse SP4 derived in conventional manner from the scan end signal SP2, which in turn is derived from one of the photosensors 45 (FIGS. 8 (b) and 8 (c)) is fed through an analogue switch S1 to discharge a capacitor C1 of a sample hold 60, (FIG. 8 (e)). The control pulse SP4 is also fed through a delay DL1 which causes an analogue switch S2 to close thus connecting the capacitor C1 to the photo-multiplier 34. It will be appreciated that the load across the resistor R1, at the point in time that the switch S2 is closed, i.e. after the inspection or scan period will be due only to leakage of ambient light. The capacitor C1 is now charged to a voltage corresponding to the ambient light transmission. This voltage is in turn fed to a differential amplifier A1 until it is discharged at the end of the next scanning or inspection period. Accordingly, the output of the differential amplifier A1 is the signal 8 (f). It should be noted that the signal 8 (f) is an inspection signal from an "acceptable" bottle.

A variable electrical signal output network 61 comprising a number of variable resistors VR3, VR4, VR5, VR6, VR7 and VR8 operatively connected to switches S3, S4, S5, S6, S7 and S8 respectively, is provided. This circuit is used to provide a variable acceptance signal 9 (d), for a specific type of container being inspected. Each of the switches S3 to S8 inclusive is a CMOS analogue switch which is controlled through a simple RS flip-flop and an adjustable delay circuit by pulses derived from the photosensors 45. The signal 9 (d) is fed through a capacitor C3 and a resistor R3, used to eliminate switching transients. The signal 9 (d) is fed to one side 63 of a diode D1 and to a differential amplifier A3. The inspection signal 8 (f) is fed through a resistor R2 to the other side 62 of the diode D1.

When the voltage signal transmitted to 62 is more negative than the voltage signal being transmitted to 63 the voltage at 62 is clamped to the potential of the voltage at 63. Accordingly, the voltage of the signal from the unity-gain buffer amplifier A2 is shown by the waveform 9 (d).

Figure 10:
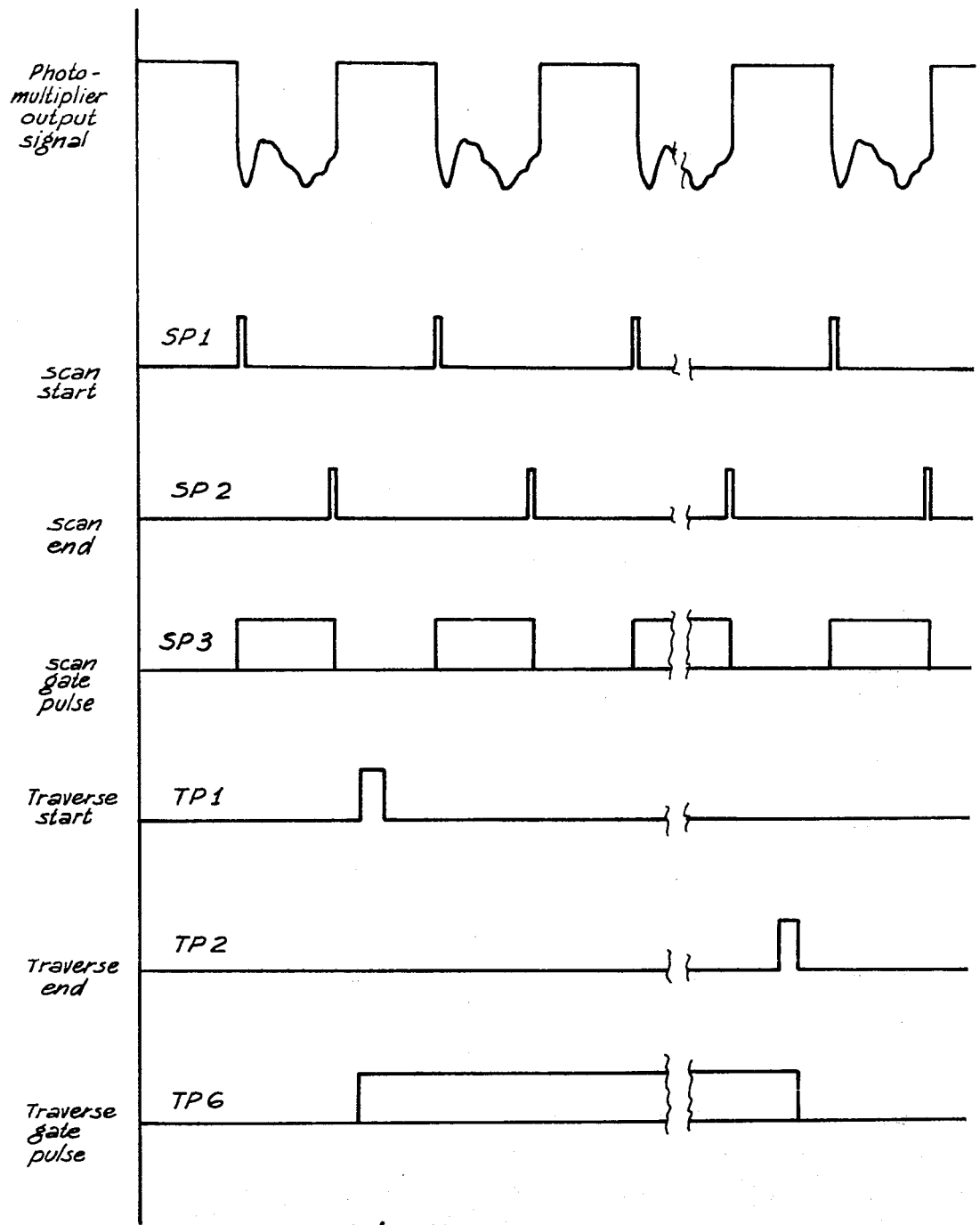
FIG. 10 is a diagram of the scan signals and some appropriate control signals generated during inspection of a translucent container.

When, however, an unacceptable container is scanned, the signal produced through the resistor R2 and hence at 62 will be the waveform 9 (a). This waveform 9 (a) will ensure that at two instances during the inspection or scanning signal, the point 62 will not be clamped to the potential of the point 63 and accordingly the waveform 9 (a) will be transmitted to the unity-gain amplifier A2 and from thence to the one input of a differential amplifier A3. The other input of the differential amplifier A3 is fed with the waveform 9 (d). Accordingly, the signal output of the differential amplifier A3 will be of the waveform 9 (e) which will be fed to the resistor R4. Thus during the actual scanning period, the output from this amplifier A3 consists only of a pair of fault signal pulses on a zero volt base line. This signal 9 (e) is in turn fed to one side 70 of a further diode D2 and is clipped in conventional manner to a peak waveform 9 (f). This waveform 9 (f) is in turn fed to a non-inverting amplifier A5 the gain of which is set by means of resistors R6 and R5, to provide an output signal of waveform 9 (g) which is fed to a gate G1. In this embodiment of the invention the output signal is 15 volts and the minimum usable value of a fault signal input pulse is approximately 0.25. Referring to FIGS. 6 and 10, the scan start signal SP1 and the scan end signal SP2 are fed to a flip-flop FF1 to form an output pulse, namely, a scan gate pulse SP3 which is fed to the gate 1.

Still referring to FIGS. 6 and 10, a traverse start pulse TP1 is fed from the timing unit 69 as is a traverse end pulse TP2 to a flip-flop FF2. The output of the flip-flop FF2, namely, a traverse gate pulse TP6 is fed to the gate G1. It will be noted that the traverse start pulse TP1 does not occur immediately but one or more preliminary scanning operations may be performed on the bottle 27. This is necessary where a correction for color is required as will be described hereinafter. The gate G1 then feeds a conventional five stage shift register 71 which in turn feeds a conventional reject control circuit 72, the output of which is connected to the reject mechanism. The timing unit 69 also feeds a control signal to the five stage shift register 71 to cause it to operate. Similarly, the timing unit feeds a signal TP4 to activate the reject control circuit 72 at the correct point in time and later sends the signal TP5 to reset the reject control circuit 72. It will be appreciated that the gate G1 will not operate unless there are three signals on it, namely, 9 (g), SP3 and TP6. A signal will then be fed from the gate G1 to the five stage shift register 71 which in turn will deliver a signal to the reject control circuit 72 which will not operate until the timing pulse TP4 is received, thus correct synchronization is maintained.

When the color density and/or wall thickness of the translucent containers vary significantly from container to container, for example, as illustrated by waveforms 8 (g), it is necessary that certain corrections must be made. Basically, it will be appreciated that either the inspection signal or the corresponding acceptance signal must be altered to an appropriate signal value such as to maintain a desired ratio between the inspection signal and the acceptance signal. In other words, if the absolute value of the scanning or inspection signal doubles, it is necessary to either halve the said absolute value of the inspection signal or alternatively double the absolute value of the acceptance signal.

Figure 7:
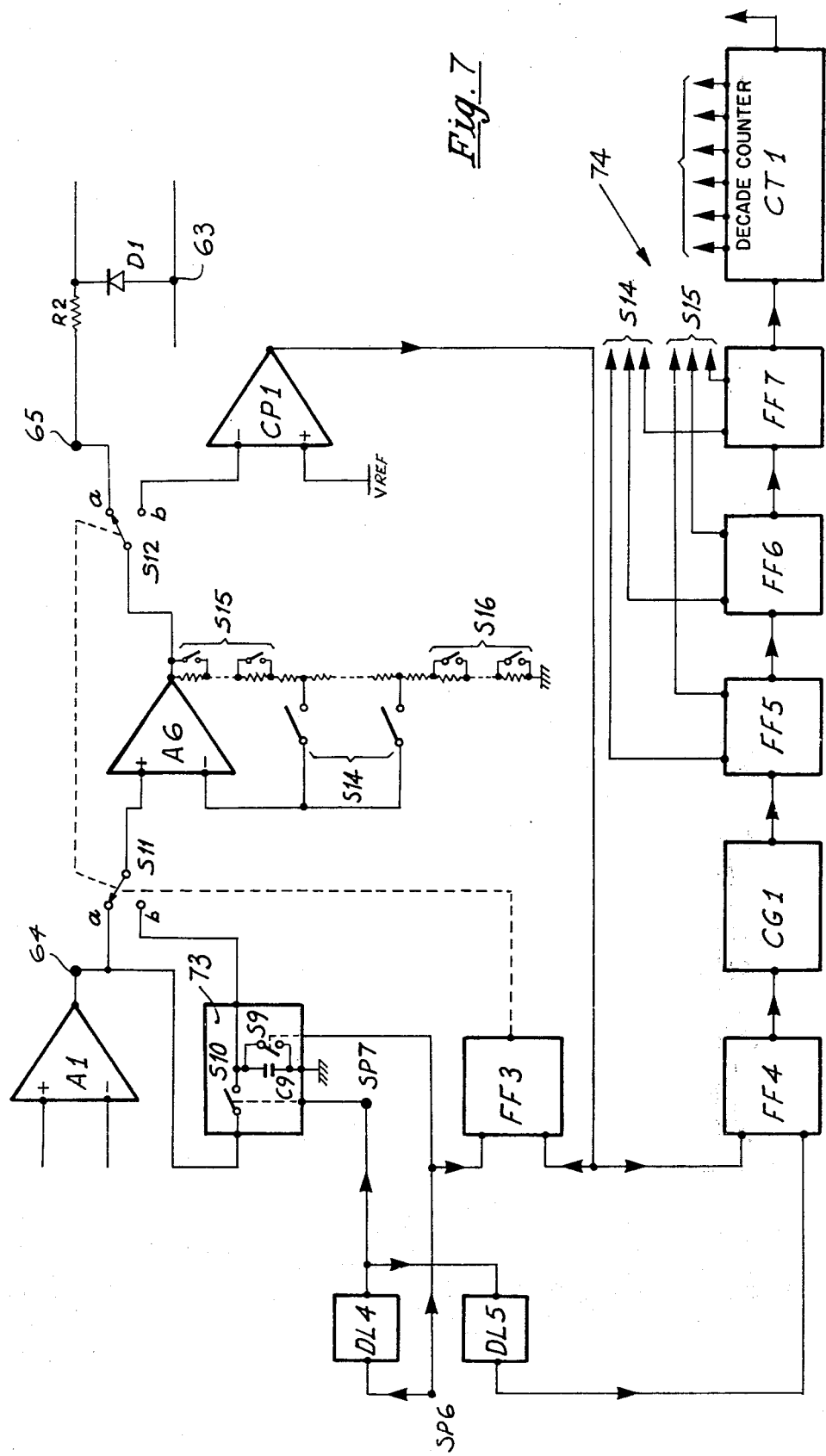
FIG. 7 is a circuit diagram of an auxiliary control circuit necessary when the colour density correction is required.

Referring to FIG. 7, there is illustrated an auxiliary control circuit inserted between the points 64 and 65 of the circuit of FIG. 6. A control pulse SP6 is developed coincident with the scan start pulse SP1. See FIG. 8 (h). The pulse SP6 is fed to a peak detector 73 comprising a pair of analogue switches S9 and S10 and capacitor C9. SP6 closes the analogue switch S9 causing the capacitor C9 to discharge, see FIG. 8 (k). The pulse SP6 is also fed to a delay DL4. The output pulse SP7 from the delay DL4 closes the switch S10, see FIG. 8 (j). The signal from the differential amplifier A1 is now fed from the point 64 to charge the capacitor C9 as illustrated in FIG. 8 (k). In FIG. 8 (g) the full line indicates the absolute value of the signal voltage 8 (g) delivered from the differential amplifier A1. To ensure correct comparison with the acceptance signal it is necessary to amplify the inspection signal to that shown by the interrupted lines. Accordingly, at the particular point in time the voltage applied to the capacitor C9 is the voltage V2, it is necessary to amplify this voltage to the voltage V3. It will be appreciated that the delay DL4 is so chosen that the detect action of the capacitor C9 occurs after a suitable time to place the sampling point at a selected vertical position on the container being scanned. The control pulse SP6 is also fed through a flip-flop FF3 to cause switches S11 and S12 to change from positions a to positions b, thus removing this auxiliary circuit from the main control circuit. The peak detector circuit 73 feeds the signal on the capacitor C9 to a variable gain amplifier A6 which in turn feeds a conventional comparator CP1 set at a suitable reference voltage, for example, 10 volts. The control pulse SP7 is also fed through a further delay DL5 to a flip-flop FF4. The flip-flop FF4 feeds a conventional clock generator CG1 which in turn feeds a divider counter chain, indicated generally by the reference numeral 74 which is of conventional construction, including flip-flops FF5, FF6 and FF7 and a decade counter CT1 which operates in a predetermined sequence. The divider counter chain 74 feeds a series of analogue switches S14, S15 and S16 which form part of the gain circuit of the variable gain amplifier A6.

In operation, the signal from the capacitor C9 is fed to the variable gain amplifier A6 and after a suitable delay the divider counter chain operates causing the gain of the variable gain amplifier A6 to be varied in value. This causes the voltage V2, that is to say, the output voltage of the capacitor C9 to be varied until it is amplified in value in excess of the base voltage of the comparator CP1 when the comparator CP1 trips. When the voltage V2 is amplified to the voltage V3, that is to say, slightly above the reference voltage of the comparator CP1 the comparator CP1 trips stopping the clock generator.

This trip action holds the switches S11, S12 and S13 in the configuration required to maintain the gain of the variable gain amplifier A6 at this gain which caused the voltage V2 to be amplified sufficiently to trip the comparator CP1. Finally, the signal from the comparator CP1 is fed to the flip-flop FF3 causing the switches S11 and S12 to be changed to their original position a. Basically, there is now an amplifier circuit between the points 64 and 65.

It will be noted that the traverse start TP1 (see FIG. 10), is not operated until some time after the first scan start signal SP1. Accordingly, the traverse gate pulse TP6 is not delivered to the gate G1 for some time after the start of the pulse SP6. Thus the rejection action of the apparatus is disabled during this initial period.

It will be appreciated that the gain of the variable gain amplifier A6 has now been so arranged to ensure that the output signal, namely, the inspection signal of the differential amplifier A1 has been amplified to ensure that the voltage is greater than a preset value. This action is repeated as each of the containers enters the inspection zone thus ensuring that the selected inspection or scan signal voltage of each container is adjusted to a predetermined value. This permits the same acceptance signal to be used despite variations in the light transmission through different containers due to color density differences and wall thickness differences.

If by any chance this sampling signal should in fact coincide with an occlusion or crack in the container, the counter CT1 is so arranged that after completing one cycle it automatically resets the flip-flops FF3, FF4, FF5, FF6 and FF7 thus returning the variable gain amplifier A6 to unity-gain and simultaneously closing the switches S11 and S12. Accordingly, when this unamplified signal is delivered from the variable gain amplifier A1, the control circuit of FIG. 6 will operate to reject the container.

In the embodiment of FIG. 7 the variable gain amplifier A6 is arranged to have a maximum gain of 4 in discrete steps of 50. The comparator CP1 trips at 10 volts. Accordingly, a signal between 2.5 volts and 10 volts delivered from the variable gain amplifier A1 can be handled by the control circuit. Thus the present circuit can handle variations of between 2.5 and 10 volts in steps of 50 that is to say, it can adjust for variations of 0.15 volts in inspection signal.

A significant variation in wall thickness or color density may be defined as that variation which would be likely to have an acceptable container rejected for no other reason than that the light transmission through the container was too low due to this variation, or that a crack or occlusion in an unacceptable container could be undetected because the mean light transmission through the container was too high.

It is envisaged that while the apparatus described in the embodiment above provides a spot beam of light adapted for scanning vertically and horizontally in the inspection zone that the invention may be applied to an apparatus in which the spot beam of light is adapted to scan vertically only.

In the embodiment described above for use when the color density and/or wall thickness to the translucent containers vary significantly from container to container the sample inspection signal was altered by an adjustment factor. It will be appreciated that in similar manner the corresponding acceptance signal could be altered by an adjustment factor so as to maintain a desired ratio between the inspection signal and the acceptance signal. It will also be appreciated that while the ambient light correction was carried out on the inspection signal that it could just as conveniently be carried out on the acceptance signal, this could be achieved by electrically adding the ambient light signal to the acceptance signal thus eliminating during inspection the effect of ambient light.

Further, it will be appreciated that the embodiment described above is merely one embodiment which the present invention could be carried out. It will be immediately apparaent to those skilled in the art, the many other ways in which the invention of the present invention could be carried out without departing from the scope of the invention.

I claim:

1. Apparatus for detecting the presence of extraneous matter and/or cracks in translucent containers, said apparatus comprising:
   an inspection zone;
   means for rotating a translucent container within the inspection zone;
   means for generating and vertically scanning a spot beam of light in the inspection zone;
   a light collection apparatus in the inspection zone;
   means for generating an electrical inspection signal corresponding to the amount of light passing through the translucent container and impinging on the light collection apparatus;
   means for synchronously generating a predetermined electrical acceptance signal the value of said acceptance signal being a function of the vertical position of the spot beam of light relative to the container, and means for comparing said inspection signal with said predetermined electrical acceptance signal; and
   means for generating a rejection signal when the intensity of light passing through the translucent container is below a predetermined value measured by the said acceptance signal.

2. Apparatus as recited in claim 1, in which the means for generating the acceptance signal includes a plurality of photosensors for sensing the vertical position of the spot beam of light, and a variable electrical signal output network connected to be controlled by said plurality of photosensors.

3. Apparatus as recited in claim 2, in which means is provided for scanning the spot beam of light vertically and horizontally in the inspection zone which means comprises;
   means for generating a vertically scanning slit of light, and projecting the latter towards the inspection zone; and
   a masking member containing a vertical slit being movable horizontally in the path of the scanning slit of light so as to occlude a portion of the latter and thereby resolve the vertical scanning slit of light into a spot beam scanning vertically and horizontally in the inspection zone.

4. Apparatus as recited in claim 3, in which there is provided;
   a drum adapted for rotation;
   a plurality of plane mirrors tangentially mounted on the drum;
   a light source adapted to project a slit of light on to the drum whereby each rotating mirror resolves the straight slit of light into a scanning slit of light;
   a cylindrical column below the drum having a vertical slot the axis of which column is perpendicular to the axis of the drum;
   a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

5. Apparatus as recited in claim 2, in which ambient light correction means is provided for determining prior to inspection the electrical signal corresponding to the effect of ambient light impinging on the light collection apparatus, and in which said ambient light signal is electrically subtracted from the inspection signal during inspection of the translucent container.

6. Apparatus as recited in claim 5, in which means is provided for scanning the spot beam of light vertically and horizontally in the inspection zone which comprises;
   means for generating a vertically scanning slit of light, and projecting the latter towards the inspection zone; and
   a masking member containing a vertical slit being movable horizontally in the path of the scanning slit of light so as to occlude a portion of the latter and thereby resolve the vertical scanning slit of light into a spot beam scanning vertically and horizontally in the inspection zone.

7. An apparatus as recited in claim 6, in which there is provided;
   a drum adapted for rotation;
   a plurality of plane mirrors tangentially mounted on the drum;
   a light source adapted to project a slit of light on to the drum whereby each rotating mirror resolves the straight slit of light into a scanning slit of light;
   a cylindrical column below the drum having a vertical slot the axis of which column is perpendicular to the axis of the drum;
   a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

8. Apparatus as recited in claim 5, in which the ambient light correction means comprises:
   a differential amplifier;
   means for feeding the inspection signal to the differential amplifier;
   a sample and hold circuit operatively connected to the light collection apparatus for holding an electrical signal corresponding to the ambient light impinging on the light collection apparatus prior to inspection; and means for feeding the said ambient light signal to the differential amplifier whereby the signal output of the amplifier is the electrical difference between the inspection signal and the ambient light signal.

9. Apparatus as recited in claim 8, in which means is provided for scanning the spot beam of light vertically and horizontally in the inspection zone which means comprises;

means for generating a vertically scanning slit of light, and projecting the latter towards the inspection zone; and a masking member containing a vertical slit being movable horizontally in the path of the scanning slit of light so as to occlude a portion of the latter and thereby resolve the vertical scanning slit of light into a spot beam scanning vertically and horizontally in the inspection zone.

10. Apparatus as recited in claim 9, in which there is provided;

a drum adapted for rotation;

a plurality of plane mirrors tangentially mounted on the drum;

a light source adapted to project a slit of light on to the drum whereby each rotating mirror resolves the straight slit of light into a scanning slit of light;

a cylindrical column below the drum having a vertical slot the axis of which column is perpendicular to the axis of the drum;

a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

11. Apparatus as recited in claim 1, in which ambient light correction means is provided for determining prior to inspection the electrical signal corresponding to the effect of ambient light impinging on the light collection apparatus, and in which said ambient light signal is electrically subtracted from the inspection signal during inspection of the translucent container.

12. Apparatus as recited in claim 11, in which the ambient light correction means comprises:

a differential amplifier;

means for feeding the inspection signal to the differential amplifier;

a sample and hold circuit operatively connected to the light collection apparatus for holding an electrical signal corresponding to the ambient light impinging on the light collection apparatus prior to inspection; and means for feeding the said ambient light signal to the differential amplifier whereby the signal output of the amplifier is the electrical difference between the inspection signal and the ambient light signal.

13. Apparatus as recited in claim 12, in which means is provided for scanning the spot beam of light vertically and horizontally in the inspection zone which means comprises;

means for generating a vertically scanning slit of light, and projecting the latter towards the inspection zone; and a masking member containing a vertical slit being movable horizontally in the path of the scanning slit of light so as to occlude a portion of the latter and thereby resolve the vertical scanning slit of light into a spot beam scanning vertically and horizontally in the inspection zone.

14. Apparatus as recited in claim 13, in which there is provided;

a drum adapted for rotation;

a plurality of plane mirrors tangentially mounted on the drum;

a light source adapted to project a slit of light on to the drum whereby each rotating mirror resolves the straight slit of light into a scanning slit of light;

a cylindrical column below the drum having a vertical slot the axis of which column is perpendicular to the axis of the drum;

a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

15. Apparatus as recited in claim 11, in which means is provided for scanning the spot beam of light vertically and horizontally in the inspection zone which means comprises;

means for generating a vertically scanning slit of of light, and projecting the latter towards the inspection zone; and a masking member containing a vertical slit being movable horizontally in the path of the scanning slit of light so as to occlude a portion of the latter and thereby resolve the vertical scanning slit of light into a spot beam scanning vertically and horizontally in the inspection zone.

16. Apparatus as recited in claim 15, in which there is provided;

a drum adapted for rotation;

a plurality of plane mirrors tangentially mounted on the drum;

a light source adapted to project a slit of light on to the drum whereby each rotating mirror resoves the straight slit of light in a scanning slit of light;

a cylindrical column below the drum having a vertical slot the axis of which column is perpendicular to the axis of the drum;

a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

17. Apparatus as recited in claim 1, in which means is provided for scanning the spot beam of light vertically and horizontally in the inspection zone which means comprises;
  means for generating a vertically scanning slit of light, and projecting the latter towards the inspection zone; and
  a masking member containing a vertical slit being movable horizontally in the path of the scanning slit of light so as to occlude a portion of the latter and thereby resolve the vertical scanning slit of light into a spot beam scanning vertically and horizontally in the inspection zone.

18. Apparatus as recited in claim 17, in which there is provided;
  a drum adapted for rotation;
  a plurality of plane mirrors tangentially mounted on the drum;
  a light source adapted to project a slit of light on to the drum whereby each rotating mirror resolves the straight slit of light into a scanning slit of light;
  a cylindrical column below the drum having a vertical slot the axis of which column is perpendicular to the axis of the drum;
  a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

19. Apparatus for detecting the presence of extraneous matter and/or cracks in translucent containers when the color density and/or wall thickness of the translucent containers vary significantly from container to container, said apparatus comprising;
  an inspection zone;
  means for rotating a translucent container within the inspection zone;
  means for generating and vertically scanning a spot beam of light in the inspection zone;
  a light collection apparatus in the inspection zone;
  means for generating an electrical inspection signal corresponding to the amount of the light passing through the translucent container impinging on the light collection apparatus;
  means for synchronously generating a predetermined electrical signal;
  means for comparing said inspection signal with a predetermined electrical acceptance signal;
  means for obtaining prior to inspection of a container, a sample inspection signal at a predetermined vertical position of the spot beam of light;
  means to adjust the same sample inspection signal to an appropriate signal value while still maintaining a desired ratio between the inspection signal and the acceptance signal at that vertical position of the spot beam of light, the ratio of the original signal to the adjusted signal providing an adjustment factor; and
  means to adjust the inspection signal or acceptance signal by the adjustment factor during the inspection of the container.

20. Apparatus as recited in claim 19, in which the means for generating an electrical acceptance signal includes means to vary the value of the electrical acceptance signal as a function of the vertical position of the spot beam of light relative to the container, said means including a plurality of sensors for determining the vertical position of the spot beam of light, and a variable electrical signal output network connected to be controlled by said plurality of sensors.

21. Apparatus as recited in claim 20, in which there is provided means to amplify the said sample inspection signal to a predetermined electrical signal value and to amplify the inspection signal during inspection by the same gain used to amplify the sample inspection signal said means comprising:
  a variable gain amplifier;
  a sample and hold circuit to store the sample inspection signal operatively connected to the variable amplifier;
  a counter operatively connected to the gain circuit of the variable gain amplifier to vary the gain of the amplifier in discrete steps;
  a signal comparator operatively connected to the variable gain amplifier and to the counter, said signal comparator being set to a predetermined base signal, whereby when the signal from the variable gain amplifier exceeds the predetermined base signal, the comparator stops the counter thus holding the gain of the amplifier; and
  means for producing an electrical rejection signal when with the variable gain amplifier set to maximum gain the comparator does not operate.

22. Apparatus as recited in claim 21, in which ambient light correction means is provided for determining prior to inspection the electrical signal corresponding to the effect of ambient light impinging on the light collection apparatus, and in which said ambient light signal is electrically subtracted from the inspection signal during inspection of the translucent container.

23. Apparatus as recited in claim 22, in which means is provided for scanning the spot beam of light vertically and horizontally in the inspection zone which means comprises;
  means for generating a vertically scanning slit of light, and projecting the latter towards the inspection zone; and
  a masking member containing a vertical slit being movable horizontally in the path of the scanning slit of light so as to occlude a portion of the latter and thereby resolve the vertical scanning slit of light into a spot beam scanning vertically and horizontally in the inspection zone.

24. Apparatus as recited in claim 23, in which there is provided;
  a drum adapted for rotation;
  a plurality of plane mirrors tangentially mounted on the drum;
  a light source adapted to project a slit of light on to the drum whereby each rotating mirror resolves the straight slit of light into a scanning slit of light;
  a cylindrical column below the drum having a vertical slot the axis of which column is perpendicular to the axis of the drum;
  a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

25. Apparatus as recited in claim 22, in which the ambient light correction means comprises:
  a differential amplifier;
  means for feeding the inspection signal to the differential amplifier;
  a sample and hold circuit operatively connected to the light collection apparatus for holding an electrical signal corresponding to the ambient light impinging on the light collection apparatus prior to inspection; and
  means for feeding the said ambient light signal to the differential amplifier whereby the signal output of the amplifier is the electrical difference between the inspection signal and the ambient light signal.

26. Apparatus as recited in claim 21, in which means is provided for scanning the spot beam of light vertically and horizontally in the inspection zone which means comprises;
  means for generating a vertically scanning slit of of light, and projecting the latter towards the inspection zone; and
  a masking member containing a vertical slit being movable horizontally in the path of the scanning slit of light so as to occlude a portion of the latter and thereby resolve the vertical scanning slit of light into a spot beam scanning vertically and horizontally in the inspection zone.

27. Apparatus as recited in claim 26, in which there is provided;
  a drum adapted for rotation;
  a plurality of plane mirrors tangentially mounted on the drum;
  a light source adapted to project a slit of light on to the drum whereby each rotating mirror resolves the straight slit of light into a scanning slit of light;
  a cylindrical column below the drum having a vertical slot the axis of which column is perpendicular to the axis of the drum;
  a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

28. Apparatus as recited in claim 20, in which means is provided for scanning the spot beam of light vertically and horizontally in the inspection zone which means comprises;
  means for generating a vertically scanning slit of light, and projecting the latter towards the inspection zone; and
  a masking member containing a vertical slit being movable horizontally in the path of the scanning slit of light so as to occlude a portion of the latter and thereby resolve the vertical scanning slit of light into a spot beam scanning vertically and horizontally in the inspection zone.

29. Apparatus as recited in claim 28, in which there is provided;
  a drum adapted for rotation;
  a plurality of plane mirrors tangentially mounted on the drum;
  a light source adapted to project a slit of light on to the drum whereby each rotating mirror resolves the straight slit of light into a scanning slit of light;
  a cylindrical column below the drum having a vertical slot the axis of which column is perpendicular to the axis of the drum;
  a plurality of plane mirrors adjustably mounted within the column at an angle to the axis of the column whereby in use the scanning slit of light is reflected from each in turn of the plane mirros so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

30. Apparatus as recited in claim 20, in which ambient light correction means is provided for determining prior to inspection the electrical signal corresponding to the effect of ambient light impinging on the light collection apparatus, and in which said ambient light signal is electrically subtracted from the inspection signal during inspection of the translucent container.

31. Apparatus as recited in claim 30, in which the ambient light correction means comprises:
  a differential amplifier;
  means for feeding the inspection signal to the differential amplifier;
  a sample and hold circuit operatively connected to the light collection apparatus for holding an electrical signal corresponding to the ambient light impinging on the light collection apparatus prior to inspection; and
  means for feeding the said ambient light signal to the differential amplifier whereby the signal output of the amplifier is the electrical difference between the inspection signal and the ambient light signal.

32. Apparatus as recited in claim 30, in which means is provided for scanning the spot beam of light vertically and horizontally in the inspection zone which means comprises;
  means for generating a vertically scanning slit of light, and projecting the latter towards the inspection zone; and
  a masking member containing a vertical slit being movable horizontally in the path of the scanning slit of light so as to occlude a portion of the latter and thereby resolve the vertical scanning slit of light into a spot beam scanning vertically and horizontally in the inspection zone.

33. Apparatus as recited in claim 32, in which there is provided;
  a drum adapted for rotation;
  a plurality of plane mirrors tangentially mounted on the drum;
  a light source adapted to project a slit of light on to the drum whereby each rotating mirror resolves the straight slit of light into a scanning slit of light;
  a cylindrical column below the drum having a vertical slot the axis of which column is perpendicular to the axis of the drum;
  a plurality of plane mirrors adjustably mounted within the column at an angle to the axis of the column whereby in sue the scanning slit of light is reflected from each in turn of the plan mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

34. Apparatus as recited in claim 19, in which there is provided, means to amplify the said sample inspection signal to a predetermined electrical signal value and to amplify the inspection signal during inspection by the same gain used to amplify the sample inspection signal said means comprising:
   a variable gain amplifier;
   a sample and hold circuit to store the sample inspection signal operatively connected to the variable gain amplifier;
   a counter operatively connected to the gain circuit of the variable gain amplifier to vary the gain of the amplifier in discrete steps;
   a signal comparator operatively connected to the variable gain amplifier and to the counter, said signal comparator being set to a predetermined base signal, whereby when the signal from the variable gain amplifier exceeds the predetermined base signal, the comparator stops the counter thus holding the gain of the amplifier; and
   means for producing an electrical rejection signal when with the variable amplifier set to maximum gain the comparator does not operate.

35. Apparatus as recited in claim 34, in which means is provided for scanning the spot beam of light vertically and horizontally in the inspection zone which means comprises;
   means for generating a vertically scanning slit of light, and projecting the latter towards the inspection zone; and
   a masking member containing a vertical slit being movable horizontally in the path of the scanning slit of light so as to occlude a portion of the latter and thereby resolve the vertical scanning slit of light into a spot beam scanning vertically and horizontally in the inspection zone.

36. Apparatus as recited in claim 35, in which there is provided;
   a drum adapted for rotation;
   a plurality of plane mirrors tangentially mounted on the drum;
   a light source adapted to project a slit of light on to the drum whereby each rotating mirror resolves the straight slit of light into a scanning slit of light;
   a cylindrical column below the drum having a vertical slot the axis of which column is perpendicular to the axis of the drum;
   a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adustable so that the angle of incidence of the spot beam of light on the container is the optimum angle for the detection of extraneous matter and cracks.

37. Apparatus as recited in claim 34, in which ambient light correction means is provided for determining prior to inspection the electrical signal corresponding to the effect of ambient light impinging on the light collection apparatus, and in which said ambient light signal is electrically added to the acceptance signal or subtracted from the inspection signal during inspection of the translucent container.

38. Apparatus as recited in claim 37, in which the ambient light correction means comprises:
   a differential amplifier;
   means for feeding the inspection signal to the differential amplifer;
   a sample and hold circuit operatively connected to to the light collection apparatus for holding an electrical signal corresponding to the ambient light impinging on the light collection apparatus prior to inspection; and
   means for feeding the said ambient light signal to the differential amplifier whereby the signal output of the amplifier is the electrical difference between the inspection signal and the ambient light signal.

39. Apparatus as recited in claim 37, in which means is provided for scanning the spot beam of light vertically and horizontally in the inspection zone which means comprises;
   means for generating a vertically scanning slit of light, and projecting the latter towards the inspection zone; and
   a masking member containing a vertical slit being movable horizontally in the path of the scanning slit of light so as to occlude a portion of the latter and thereby resolve the vertical scanning slit of light into a spot beam scanning vertically and horizontally in the inspection zone.

40. Apparatus as recited in claim 39, in which there is provided;
   a drum adapted for rotation;
   a plurality of plane mirrors tantentially mounted on the drum;
   a light source adapted to project a slit of light on to the drum whereby each rotating mirror resolves the straight slit of light into a scanning slit of light;
   a cylindrical column below the drum having a vertical slot the axis of which column is perpendicular to the to the axis of the drum;
   a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

41. Apparatus as recited in claim 19, in which ambient light correction means is provided for determining prior to inspection the electrical signal corresponding to the effect of ambient light impinging on the light collection apparatus, and in which said ambient light signal is electrically subtracted from the inspection signal during inspection of the translucent container.

42. Apparatus as recited in claim 41, in which the ambient light correction means comprises:
   a differential amplifier;
   means for feeding the inspection signal to the differential amplifier;
   a sample and hold circuit operatively connected to the light collection apparatus for holding an electrical signal corresponding to the ambient light impinging on the light collection apparatus prior to inspection; and means for feeding the said ambient light signal to the differential amplifier whereby the signal output of the amplifier is the electrical difference between the inspection signal and the ambient light signal.

43. Apparatus as recited in claim 41, in which means is provided for scanning the spot beam of light vertically and horizontally in the inspection zone which means comprises;

means for generating a vertically scanning slit of light, and projecting the latter towards the inspection zone; and a masking member containing a vertical slit being movable horizontally in the path of the scanning slit of light so as to occlude a portion of the latter and thereby resolve the vertical scanning slit of light into a spot beam scanning vertically and horizontally in the inspection zone.

44. Apparatus as recited in claim 43, in which there is provided;

a drum adapted for rotation;

a plurality of plane mirrors tangentially mounted on the drum;

a light source adapted to project a slit of light on to the drum whereby each rotating mirror resolves the straight slit of light into a scanning slit of light;

a cylindrical column below the drum having a vertical slot the axis of which column is perpendicular to the axis of the drum;

a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

45. Apparatus as recited in claim 19, in which means is provided for scanning the spot beam of light vertically and horizontally in the inspection zone which comprises;

means for generating a vertically scanning slit of light, and projecting the latter towards the inspection zone; and a masking member containing a vertical slit being movable horizontally in the path of the scanning slit of light so as to occlude a portion of the latter and thereby resolve the vertical scanning slit of light into a spot beam scanning vertically and horizontally in the inspection zone.

46. Apparatus as recited in claim 45, in which there is provided;

a drum adapted for rotation;

a plurality of plane mirrors tangentially mounted on the drum;

a light source adapted to project a slit of light on to the drum whereby each rotating mirror resolves the straight slit of light into a scanning slit of lights;

a cylindrical column below the drum having a vertical slot the axis of which column is perpendicular to the axis of the drum;

a plurality of plane mirrors adjustably mounted within the column at an angle to the axis of the column whereby in use the scanning slit of light is reflected from each in turn of the plane mirrors so as to pass through the vertical slot in the column towards the inspection zone, the inclination of the reflective surface of each mirror to the vertical axis of the column is adjustable so that the angle of incidence of the spot beam of light on the container is the optimum angle for the detection of extraneous matter and cracks.

47. A method for detecting the presence of extraneous matter and/or cracks in translucent containers said method including the steps of:

moving the translucent container into an inspection zone;

rotating the container about its vertical axis within the inspection zone;

vertically scanning the container within the inspection zone with a spot beam of light;

collecting the light transmitted through the container in the inspection zone;

generating an electrical inspection signal corresponding the intensity of light passing through the container;

providing an acceptance signal which is a function of the vertical position of the spot beam of light relative to the container;

comparing said inspection with signal with said acceptance signal; and generating a rejection signal when the intensity of light passing through the translucent container is below a predetermined value measured by said acceptance signal.

48. A method as recited in claim 47, in which the following additional steps are carried out;

obtaining an electrical signal corresponding to the ambient light prior to inspection; and subtracting said ambient light signal from the inspection signal during inspection of the translucent container.

49. A method as recited in claim 47, in which the following steps prior to inspection are carried out;

a sample inspection signal on a predetermined vertical position of the spot beam of light relative to the container is obtained;

the said sample inspection signal is adjusted to an appropriate signal value, said adjustment determining an adjustment factor which is the ratio of the original to the adjusted signal, such as to maintain a desired ratio between the inspection signal and the acceptance signal;

adjusting the inspection signal or acceptance signal by the adjustment factor during the inspection of the container.

50. A method as recited in claim 49, in which the following additional steps are carried out;

obtaining an electrical signal corresponding to the ambient light prior to inspection; and subtracting said ambient light signal from the insepction signal during inspection of the translucent container.

51. A method as recited in claim 47, in which the acceptance signal is generated by detecting the vertical position of the spot beam of light relative to the container, and by generating an electrical signal corresponding to the vertical position of the spot beam of light which latter electrical signal activates a variable electrical signal output network.

52. A method as recited in claim 51, in which the following additional steps are carried out;
  obtaining an electrical signal corresponding to the ambient light prior to inspection; and
  subtracting said ambient light signal from the inspection signal during inspection of the translucent container.

53. A method as recited in claim 51, in which the following steps prior to inspection are carried out;
  a sample inspection signal on a predetermined vertical position of the spot beam of light relative to the container is obtained;
  the said sample inspection signal is adjusted to an appropriate signal value, said adjustment determining an adjustment factor which is the ratio of the original to the adjusted signal, such as to maintain a desired ratio between the inspection signal and the acceptance signal;
  adjusting the inspection signal or acceptance signal by the adjustment factor during the inspection of the container.

54. A method as recited in claim 53, in which the following additional steps are carried out;
  obtaining an electrical signal corresponding to the ambient light prior to inspection; and
  subtracting said ambient light signal from the inspection signal during inspection of the translucent container.

* * * * *